(12) United States Patent
Keefer et al.

(10) Patent No.: US 8,535,323 B2
(45) Date of Patent: Sep. 17, 2013

(54) CONSTRAINING RING INSERTER

(75) Inventors: Ryan C. Keefer, Fort Wayne, IN (US);
Larry G. McCleary, Warsaw, IN (US);
Robert B. Brigham, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 1326 days.

(21) Appl. No.: 12/011,233

(22) Filed: Jan. 25, 2008

(65) Prior Publication Data
US 2009/0192626 A1    Jul. 30, 2009

(51) Int. Cl.
| | |
|---|---|
| *A61B 17/58* | (2006.01) |
| *A61B 17/60* | (2006.01) |
| *A61F 2/00* | (2006.01) |
| *B23P 19/04* | (2006.01) |
| *B60P 1/48* | (2006.01) |
| *B25B 5/06* | (2006.01) |
| *B43L 5/02* | (2006.01) |
| *H01L 21/687* | (2006.01) |
| *B21B 25/00* | (2006.01) |
| *B25C 3/00* | (2006.01) |

(52) U.S. Cl.
USPC ............. 606/91; 606/99; 29/229; 254/10.5; 269/254 R; 72/465.1; 81/44

(58) Field of Classification Search
USPC .............. 81/176.3, 13, 44; 403/325; 30/338; 606/91, 99; 294/33, 90, 99.1, 119.2, 99.2, 294/166; 248/575; 29/229, 224, 225, 230; 254/10.5; 72/465.1, 466.9; 269/254 R
See application file for complete search history.

(56) References Cited

U.S. PATENT DOCUMENTS

| | | | | | |
|---|---|---|---|---|---|
| 327,394 | A | * | 9/1885 | Hemsley | 294/99.2 |
| 612,813 | A | * | 10/1898 | Bickford | 294/100 |
| 902,726 | A | * | 11/1908 | Greer | 294/99.2 |
| 1,200,158 | A | * | 10/1916 | Barrett | 81/487 |
| 1,520,227 | A | * | 12/1924 | DeVitalis | 294/99.2 |
| 1,596,678 | A | * | 8/1926 | Miller | 29/270 |
| 1,658,145 | A | * | 2/1928 | Uyei | 294/19.2 |
| 1,874,257 | A | * | 8/1932 | Doptis | 29/213.1 |
| 2,075,217 | A | * | 3/1937 | Milburn | 215/395 |
| 2,483,379 | A | * | 9/1949 | Brell | 29/229 |
| 2,562,071 | A | * | 7/1951 | Stueland | 81/53.12 |
| 2,650,722 | A | * | 9/1953 | Stabile | 221/220 |
| 2,722,148 | A | * | 11/1955 | Woyton | 294/99.2 |
| 2,735,581 | A | * | 2/1956 | Erdmann | 221/220 |
| 2,810,601 | A | * | 10/1957 | Tydings | 294/33 |
| 2,829,548 | A | * | 4/1958 | Byrd | 29/270 |

(Continued)

FOREIGN PATENT DOCUMENTS

| | | |
|---|---|---|
| EP | 1493406 | 1/2005 |
| EP | 1738723 A1 | 1/2007 |

*Primary Examiner* — Kevin T Truong
*Assistant Examiner* — David Bates
(74) *Attorney, Agent, or Firm* — Maginot, Moore & Beck, LLP

(57) ABSTRACT

A hand held instrument is provided in one embodiment in a kit for use in positioning a constraining ring of an acetabular liner system and includes a shaft including a first coupling member, and a plurality of heads, each of the plurality of heads including (i) a base configured to couple with the first coupling member and (ii) a pair of resilient gripper arms, each of the pair of resilient gripper arms defining a constraining ring reception area having a size different from the constraining ring reception area defined by the pair of gripper arms of each of the other of the plurality of heads.

15 Claims, 8 Drawing Sheets

(56) References Cited

U.S. PATENT DOCUMENTS

| | | | | |
|---|---|---|---|---|
| 2,900,107 A * | 8/1959 | Erdmann | | 221/220 |
| 2,906,433 A * | 9/1959 | Erdmann | | 221/220 |
| 2,978,802 A * | 4/1961 | Erdmann | | 29/229 |
| 3,470,600 A * | 10/1969 | Hosbach | | 29/243.57 |
| 3,857,389 A * | 12/1974 | Amstutz | | 606/86 R |
| 4,256,157 A * | 3/1981 | Grayson | | 81/44 |
| 4,422,489 A * | 12/1983 | Ross | | 81/44 |
| 4,663,996 A * | 5/1987 | Grudgfield et al. | | 81/53.11 |
| 4,676,798 A | 6/1987 | Noiles | | |
| 4,784,025 A * | 11/1988 | Peck | | 81/44 |
| 4,841,819 A * | 6/1989 | Williams | | 81/3.8 |
| 4,873,754 A * | 10/1989 | Gleasman | | 29/229 |
| 5,125,296 A * | 6/1992 | Nelson et al. | | 81/9.3 |
| 5,169,399 A * | 12/1992 | Ryland et al. | | 606/91 |
| 5,171,243 A * | 12/1992 | Kashuba et al. | | 606/86 R |
| 5,334,215 A * | 8/1994 | Chen | | 606/210 |
| 5,387,019 A * | 2/1995 | Britzke, II | | 294/2 |
| 5,540,697 A * | 7/1996 | Rehmann et al. | | 606/91 |
| 5,700,046 A * | 12/1997 | Van Doren et al. | | 294/119.1 |
| 5,800,555 A | 9/1998 | Gray, III | | |
| 6,125,517 A * | 10/2000 | Yu | | 29/229 |
| 6,132,469 A | 10/2000 | Schroeder | | |
| 6,159,215 A * | 12/2000 | Urbahns et al. | | 606/86 R |
| 6,402,789 B1 * | 6/2002 | Gramnas | | 623/38 |
| 6,409,453 B1 * | 6/2002 | Brodine et al. | | 414/416.01 |
| 6,440,142 B1 * | 8/2002 | Ralph et al. | | 606/99 |
| 6,488,713 B1 | 12/2002 | Hershberger | | |
| 6,578,893 B2 * | 6/2003 | Soucy et al. | | 294/99.1 |
| 7,022,142 B2 | 4/2006 | Johnson | | |
| 7,089,640 B2 * | 8/2006 | Tanaka et al. | | 29/229 |
| 7,115,145 B2 | 10/2006 | Richards | | |
| 7,169,186 B2 | 1/2007 | Harris et al. | | |
| 7,727,282 B2 * | 6/2010 | Slone et al. | | 623/22.12 |
| 2003/0047040 A1 * | 3/2003 | Goskesen | | 81/13 |
| 2003/0187512 A1 | 10/2003 | Frederick et al. | | |
| 2005/0177172 A1 | 8/2005 | Acker et al. | | |
| 2005/0262677 A1 * | 12/2005 | Tanaka et al. | | 29/229 |
| 2007/0005144 A1 | 1/2007 | Leisinger et al. | | |
| 2007/0010825 A1 | 1/2007 | Leisinger et al. | | |
| 2007/0213833 A1 | 9/2007 | Mears et al. | | |
| 2007/0219562 A1 | 9/2007 | Slone et al. | | |
| 2008/0033444 A1 * | 2/2008 | Bastian et al. | | 606/85 |

* cited by examiner

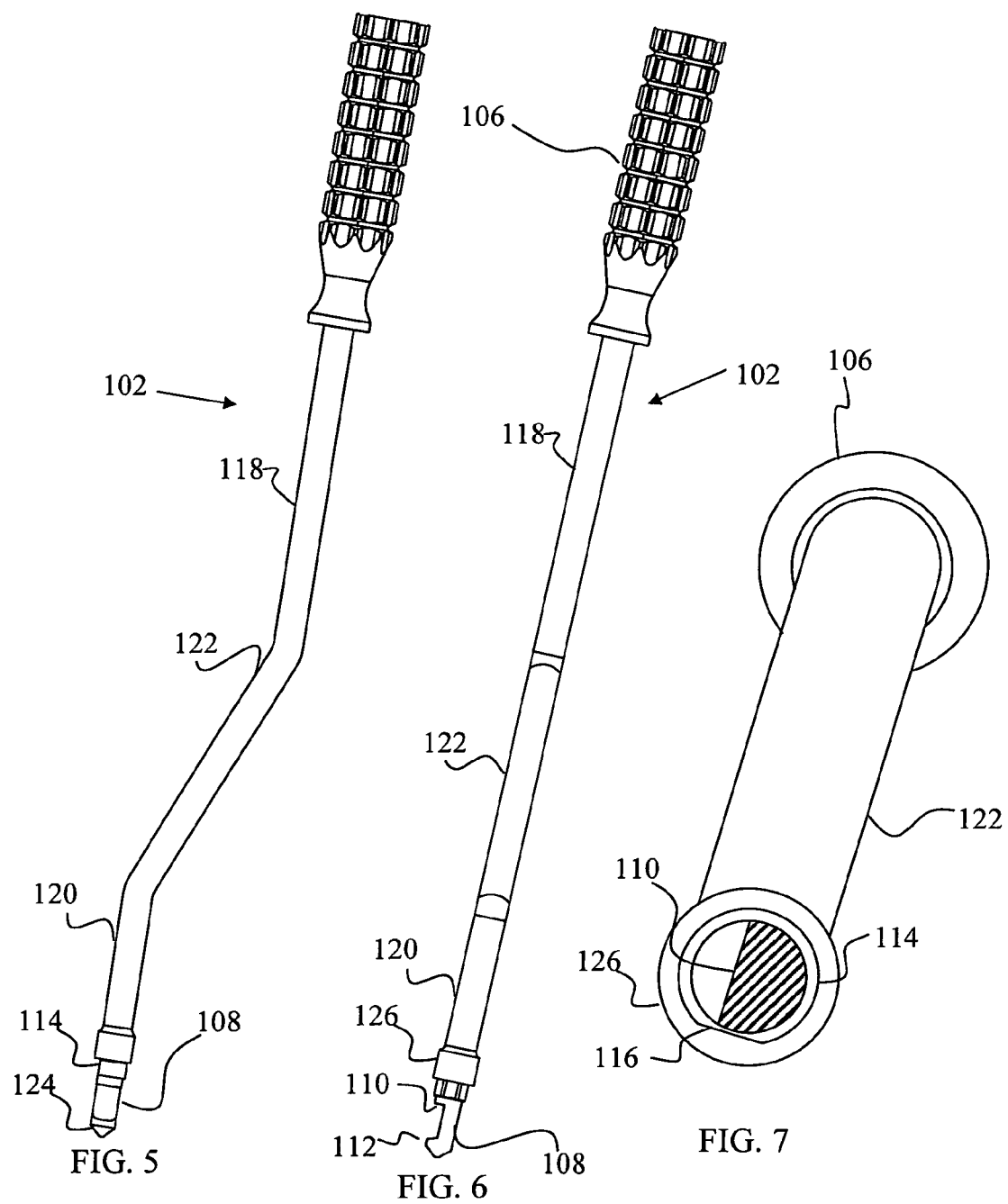

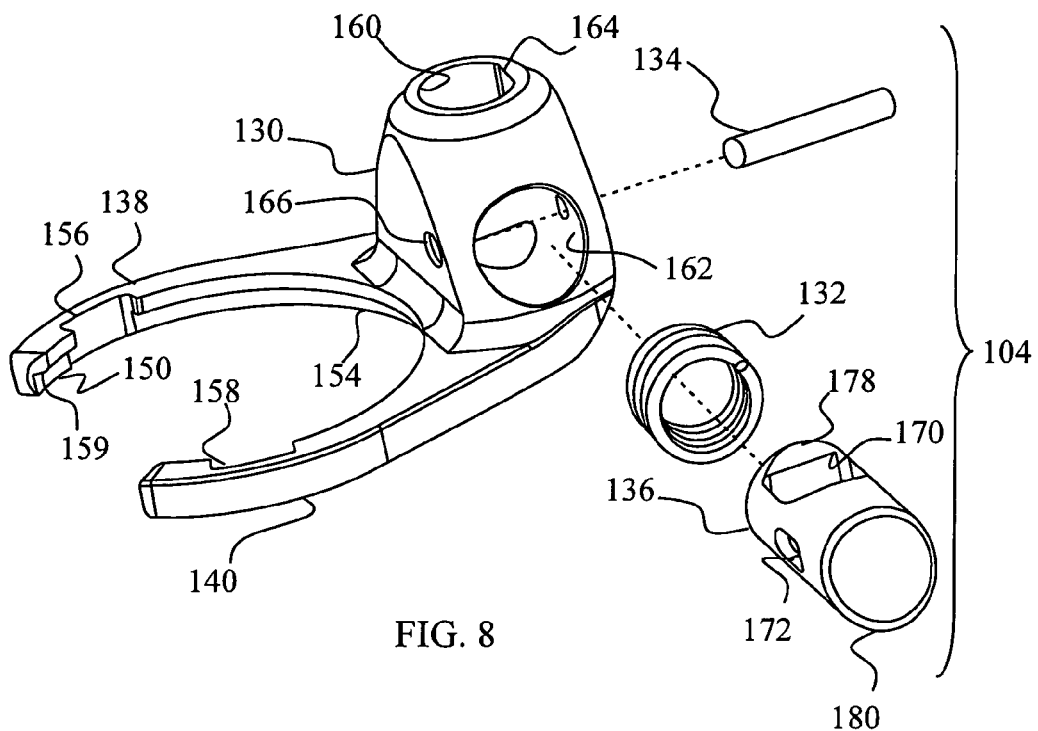
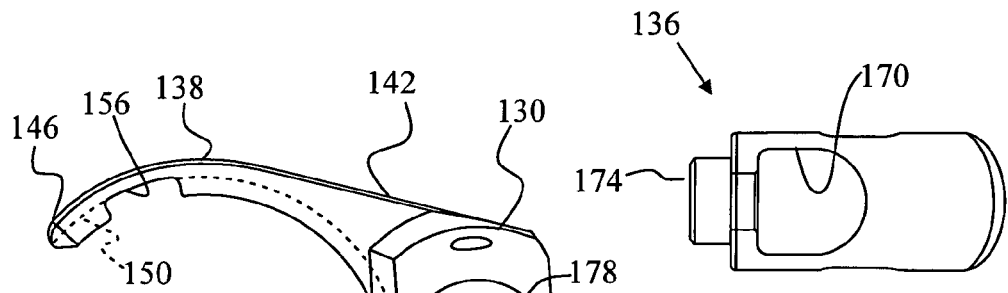
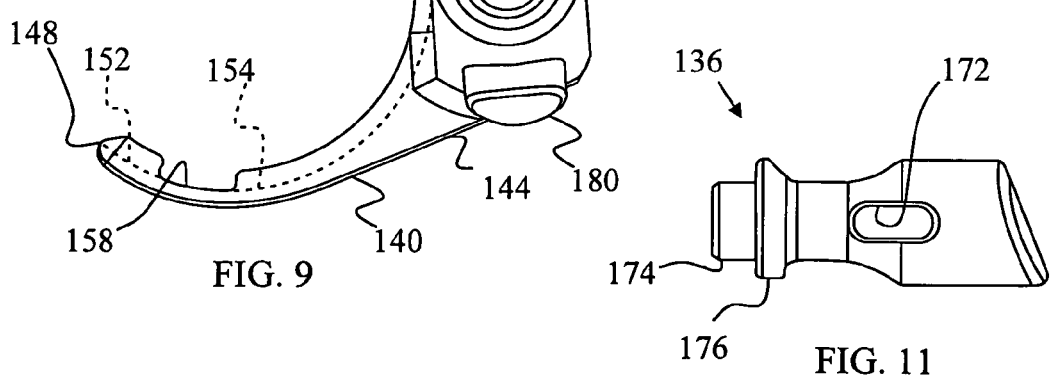

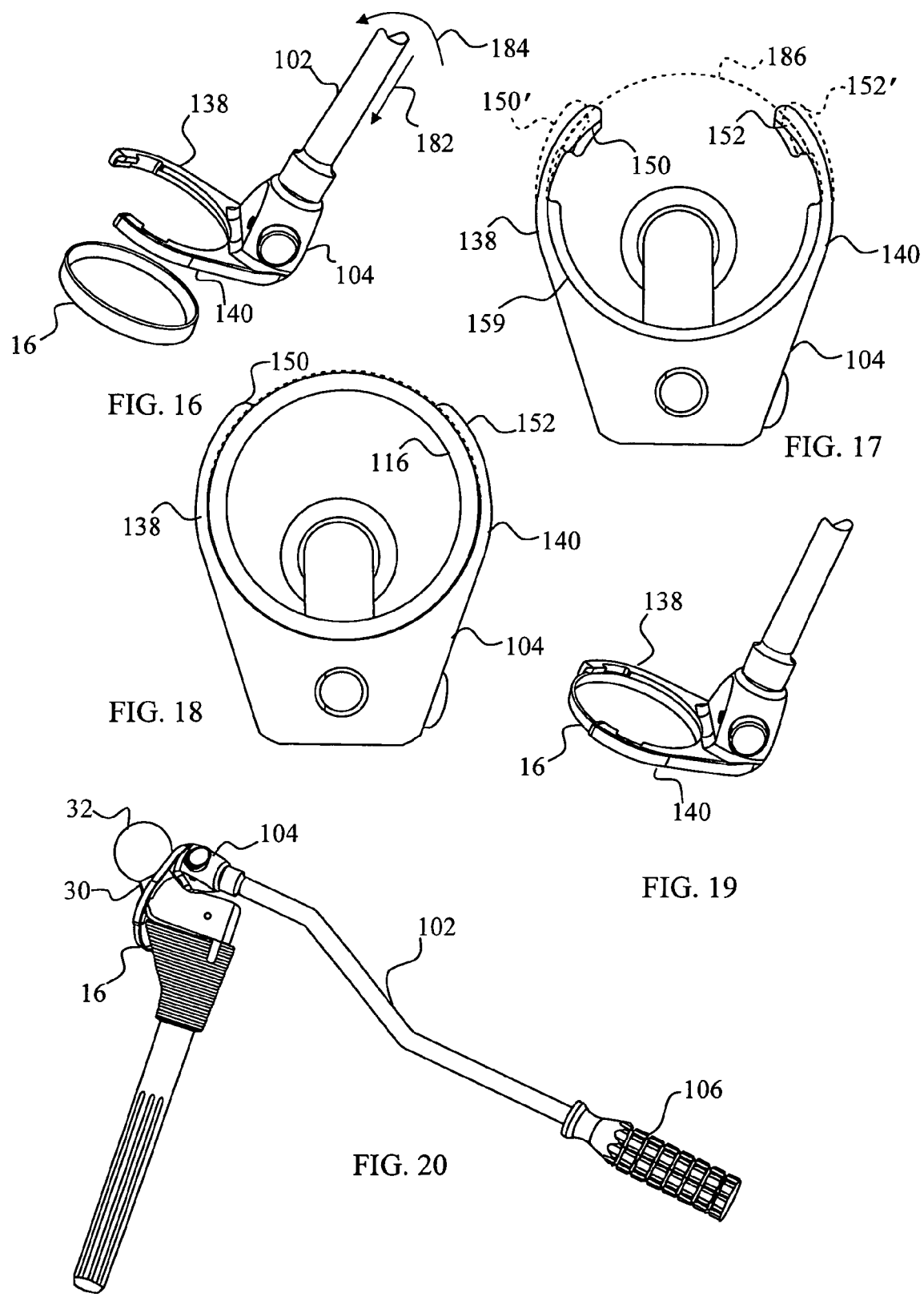

CONSTRAINING RING INSERTER

FIELD OF THE INVENTION

The present invention relates to surgical instruments, and particularly to an instrument for positioning a constraining ring for an acetabular insert.

BACKGROUND OF THE INVENTION

Joint arthroplasty is a well known surgical procedure by which a diseased and/or damaged natural joint is replaced by a prosthetic joint. Joint arthroplasty is commonly performed for hips, knees, elbows, and other joints. The health and condition of the joint to be replaced dictate the type(s) of prosthesis necessary to replace the natural joint. The hip joint includes the acetabulum of the pelvis which receives the head or ball of a femoral component. Replacement of the acetabulum is necessary when there is an inadequate articulation surface for a head or ball of a femoral component, natural or prosthetic. Prosthetic components that are used in a hip arthroplasty include acetabular cups and acetabular liners. An acetabular cup is implanted in the acetabular cavity in the pelvis to replace the natural acetabulum and the liner provides the bearing surface.

FIG. 1 shows an exemplary acetabular replacement system 10 including an acetabular cup 12, an acetabular liner 14 and a constraining ring 16. The acetabular cup 12 includes a cavity 18 which is configured to receive the acetabular liner 14. The acetabular liner 14 includes an outer surface 20 configured to be received by the cavity 18 and a lip 22 defining an opening to a cavity 24.

The acetabular system 10 may be used with a femoral system 26 shown in FIG. 2. The femoral system 26 includes a stem 28, a neck 30 and a femoral ball 32. The cavity 24 is configured to receive the femoral ball 32. The cavity 24 is slightly more than a hemispherical cavity and the diameter defined by the lip 22 is less than the diameter of the femoral ball 32. Thus, once the femoral ball 32 is received into the cavity 24, the potential for inadvertent dislocation of the hip joint is reduced. In order to allow the ball 32 to be positioned within the cavity 24, the lip 22 is somewhat flexible. The constraining ring 16 is positioned over the lip 22 to restrict flexure of the lip 22 after the ball 32 is positioned within the cavity 24.

To implant an acetabular cup such as the acetabular cup 12, a cavity is reamed in the pelvis of a patient. The reamed cavity generally conforms to the outer surface of the acetabular cup 12. The acetabular cup 12 is then inserted into the formed cavity and secured to the native bone. The acetabular cup 12 is positioned in the pelvis at a fixed orientation in the acetabulum so as to emulate the patient's natural anatomy. The implanted cup 12 should remain stable to prevent erosion of the surrounding bone and to inhibit generation of excessive wear debris in the prosthetic joint.

Various methods and techniques have been used to secure an acetabular cup within a formed acetabular cavity. One such method includes the use of bone cement to secure the acetabular cup to the acetabulum. Another technique utilizes an acetabular cup having holes for receiving screws, or other types of fasteners, to affix the acetabular cup to bone. A further method includes the implantation of an acetabular cup having an outer surface with various surface features to enhance fixation of the cup within the acetabular cavity. Two or more of these methods may be used in conjunction with each other to secure the acetabular cup to the acetabulum.

No matter which technique(s) are used to secure the acetabular cup, proper initial positioning of the acetabular cup within the reamed cavity is critical to the proper functioning of the prosthetic component. The positioning of the cup is complicated by the fact that incisions used in hip or femoral operations may be quite deep, with the implantation site remote from the initial incision location. Moreover, it is desired to keep the incision as small as possible both for improved healing as well as aesthetic purposes.

Next, the liner 14 is inserted into the acetabular cup 12. The liner 14 acts as a bearing surface against which the ball or head of the femoral component presses. The implantation of a liner presents many of the same difficulties as the implantation of a cup. The instruments used to keep the incision site open crowd the incision area and obscure the surgeon's vision. Thus, the liner must be manipulated into position in a very confined space. Moreover, care must be taken to ensure that no tissue is trapped between the acetabular cup and the acetabular liner as the liner is being inserted. Obviously, obscuring the vision of the surgeon hinders the procedure and can result in undesired delays.

Once the acetabular line 14 is positioned within the acetabular cup 12, the surgeon performs a range of motion procedure to verify that the acetabular cup 12 and liner 14 are properly positioned. The range of motion procedure involves insertion of the femoral ball 32 into the cavity 24 and manipulation of the patient's leg through various positions. When the range of motion procedure is satisfactorily completed, the surgeon inserts the constraining ring 16 onto the acetabular lip 22, thereby inhibiting the ability of the lip 22 to flex. Accordingly, the femoral head 32 is constrained within the acetabular liner 14.

Manipulation of the constraining ring 16 implicates many difficulties which are similar to the difficulties in placing an acetabular cup or an acetabular liner. Additional difficulties, however, are presented due to the manner in which the constraining liner must be positioned. In order to position the constraining ring 16 on the lip 22, the constraining ring 16 must be pre-positioned on the neck 30 as shown in FIG. 3 prior to positioning the femoral ball 32 into the cavity 24. Accordingly, the constraining ring must be located within the surgical site while the femoral component 26 and the acetabular system 10 are manipulated. Thus, any device used to install the constraining ring could further encumber the manipulation of the femoral component and the acetabular component thereby delaying the procedure.

Additionally, the actual insertion of the constraining ring is difficult and awkward. Thus, the polyethylene liner may be inadvertently damaged, further delaying the procedure.

What is needed therefore is an apparatus and method for positioning a constraining ring on an acetabular liner which overcomes one or more of the above-mentioned disadvantages.

SUMMARY OF THE INVENTION

In one embodiment of the invention, a hand held instrument kit for use in positioning a constraining ring of an acetabular liner system includes a shaft including a first coupling member, and a plurality of heads, each of the plurality of heads including (i) a base configured to couple with the first coupling member and (ii) a pair of resilient gripper arms, each of the pair of resilient gripper arms defining a constraining ring reception area having a size different from the constraining ring reception area defined by the pair of gripper arms of each of the other of the plurality of heads.

In a further embodiment, a hand held instrument system for insertion of a constraining ring onto an acetabular liner includes a shaft including a first coupling member, and at least one base member including a second coupling member for coupling with the first coupling member and a third coupling member configured to couple with a constraining ring.

In another embodiment, a kit for a hand held instrument used in positioning a constraining ring of an acetabular liner system includes a shaft, a first base at an end portion of the shaft, a first seating portion defined by a portion of the perimeter of a first cylinder having a diameter similar to the diameter of the constraining ring, and a first pair of arms extending outwardly from the first base, each of the first pair of arms including a portion of the first seating portion and including a gripper portion configured to extend within the perimeter of the first cylinder in an un-flexed condition and to be resiliently positioned outwardly of the perimeter of the first cylinder in a flexed condition.

BRIEF DESCRIPTION OF THE DRAWINGS

FIG. 5 depicts a side plan view of the shaft of the constraining ring inserter system of FIG. 4;

FIG. 6 depicts a front plan view of the shaft of the constraining ring inserter system of FIG. 4 showing the indent of the coupler of the shaft;

FIG. 7 depicts a cross sectional view of shaft of the constraining ring inserter system of FIG. 4 taken through the indent;

FIG. 8 depicts a side perspective exploded view of the head of the constraining ring inserter system of FIG. 4 showing a base, a retaining pin, a spring and a shuttle incorporating principles of the invention;

FIG. 9 depicts a top plan view of the head of FIG. 8 with the spring and restraining pin installed and the shuttle partially positioned within one of the bores of the base;

FIG. 10 depicts a top plan view of the shuttle of FIG. 8 showing a coupling bore, a lip and a plunger;

FIG. 11 depicts a side plan view of the shuttle of FIG. 8 showing a retaining pin slot, the flange and the plunger;

FIG. 16 depicts a perspective view of the constraining ring inserter system of FIG. 4 positioned above a constraining ring of FIG. 1;

FIG. 17 depicts a bottom plan view of the constraining ring inserter system of FIG. 4 showing flexure of the gripper portions of the arms in an outwardly direction to receive a constraining ring;

FIG. 18 depicts a bottom plan view of the constraining ring inserter system of FIG. 4 coupled with the constraining ring of FIG. 1

FIG. 19 depicts a perspective view of the constraining ring inserter system of FIG. 4 coupled with the constraining ring of FIG. 1;

FIG. 20 depicts a perspective view of the constraining ring inserter system of FIG. 4 coupled with the constraining ring of FIG. 1 with the constraining ring positioned on the neck of the femoral component of FIG. 1.

DESCRIPTION

Figure 1:
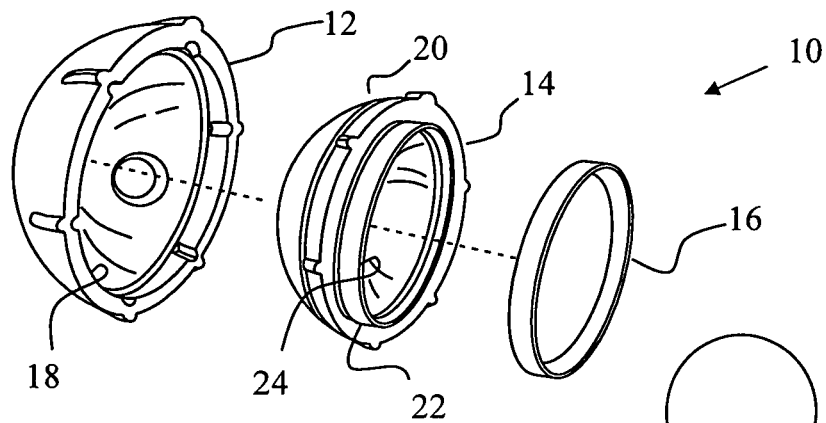
FIG. 1 depicts a perspective view of an exemplary acetabular cup, an acetabular liner and a constraining ring of the prior art.
Figure 2:
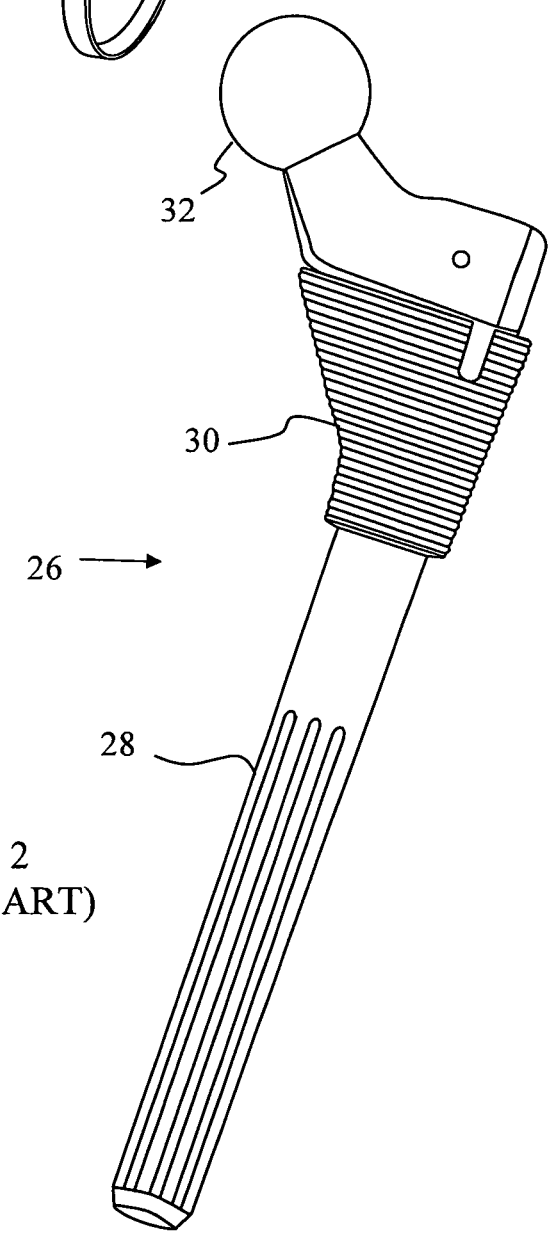
FIG. 2 depicts an side elevational view of a femoral component of the prior art.
Figure 3:
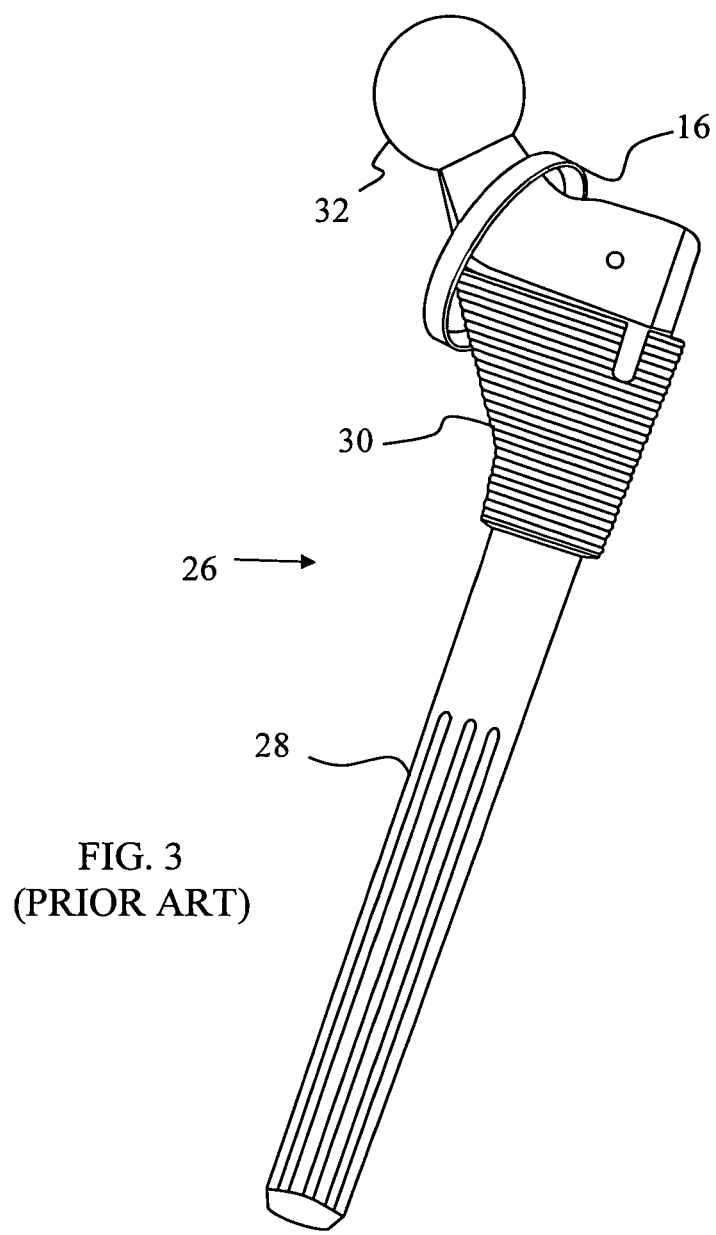
FIG. 3 depicts a perspective view of the constraining ring of FIG. 1 positioned on the neck of the femoral component of FIG. 2.

For the purposes of promoting an understanding of the principles of the invention, reference will now be made to the embodiments illustrated in the drawings and described in the following written description. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 4:
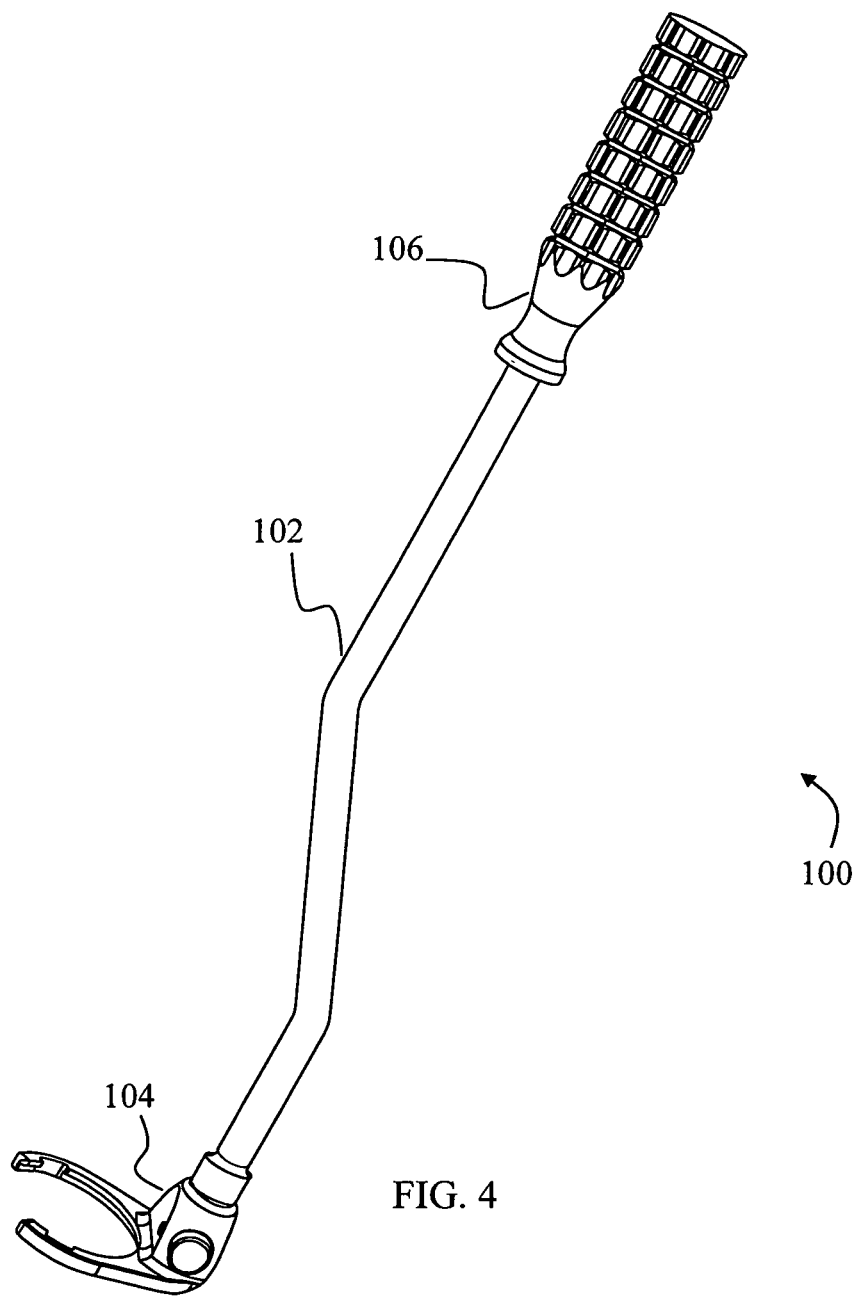
FIG. 4 depicts a perspective view of a constraining ring inserter system in accordance with principles of the invention.

Referring generally to FIG. 4, a perspective view of a constraining ring inserter system 100 for positioning a constraining ring onto an acetabular liner is shown. The inserter system 100 includes a shaped shaft 102 and a head 104. The shaft 102, also shown in plan view in FIGS. 5 and 6, is connected at one end to a handle 106. A coupling member 108 is located at the opposite end of the shaft 102. The coupling member 108 includes an indent 110 and a lip 112. A guide portion 114 located above the coupling member 108 includes a flat portion 116 as shown in FIG. 7 which is a cross sectional view of the shaft 102 taken through the indent 110.

The shaft 102 further includes an upper portion 118 that extends outwardly from the handle 106 and a lower portion 120 that is substantially parallel to but offset from the axis of the upper portion 118. A middle portion 122 of the shaft 102 extends between the upper portion 118 and the lower portion 120. The axis of the middle portion 122 in this embodiment forms an angle with both the axis of the upper portion 118 and the axis of the lower portion 120. In the embodiment of FIGS. 4-7, the angle is selected to be in the range of about 15 degrees to about 30 degrees. In one embodiment, an angle of 22.5 degrees is selected. A beveled portion 124 is located at the end of the shaft 102 opposite to the handle 106 and an enlarged portion 126 is located between the coupling member 108 and the lower portion 120 of the shaft.

In the embodiment of FIGS. 4-6, the handle 106 is formed separately from the shaft 102 while the beveled portion 124, the enlarged portion 126 and the coupling member 108 are integrally formed with the shaft 102. Any or all of these components may alternatively be formed integrally or separately.

Referring to FIGS. 8-9, the head 104 includes a base 130, a spring 132, a retaining pin 134, a shuttle 136 and a pair of arms 138 and 140. The proximal portions 142 and 144 of the arms 138 and 140 are joined to the base 130 while the distal portions 146 and 148 of the arms 138 and 140 are spaced apart from each other.

Gripper portions 150 and 152 are separated from a seating portion 154 by notches 156 and 158, respectively. A ledge 159 extends above both of the gripper portions 150 and 152 and the seating portion 154. The opposing faces of the gripper portions 150 and 152 along with the seating portion 154 thus define a constraining ring reception area between the arms 138 and 140.

Figure 12:
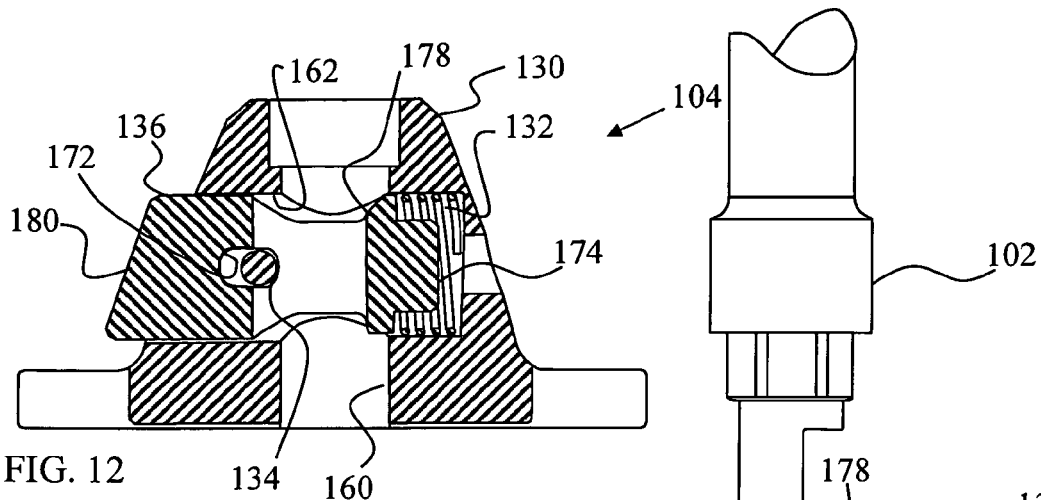
FIG. 12 depicts a cross sectional view of the head of FIG. 8 with the spring and restraining pin installed and the shuttle partially positioned within one of the bores of the base.

The base 130 includes a bore 160 and a bore 162 which intersect within the base 130. The bore 160 includes a flat portion 164 located above the intersection with the bore 162. A retaining pin bore 166 also intersects the bore 162. As shown in FIG. 12, the bores 160 and 162 are generally perpendicular. In alternative embodiments, the bores may intersect in a non-perpendicular manner. In those embodiments, the cooperative shapes of the shuttle and the coupling portion of the shaft provide a keying function such that the heads and shaft are coupled in a predetermined orientation.

The shuttle 136, also shown in FIGS. 10 and 11, includes a coupling bore 170 and a travel limiting slot 172. One end of the shuttle 136 includes a plunger 174 and a flange 176. A lip 178 is located adjacent to the flange 176 and the coupling bore 170. The opposite end of the shuttle 136 is formed as a button 180.

When the head 104 is assembled as shown in FIG. 12, the spring 132 is positioned within the bore 162. The button 180 of the shuttle 136 extends outwardly from the base 130. The remainder of the shuttle 136 is positioned within the bore 162 with the plunger 174 located within the spring 132 and the flange 176 abutting the spring 132. The spring 132 is somewhat compressed, providing a bias to the shuttle 136 in a direction outwardly from the bore 162. The shuttle 136 is maintained partially within the bore 162 by the retaining pin 134 which extends through retaining pin bore 166 and the travel limiting slot 172.

The length of the travel limiting slot 172 is selected such that when the spring 132 biases the shuttle 136 such that the retaining pin 134 contacts the end portion of the travel limiting slot 172 closest to the spring 132, the lip 178 is positioned partially within the bore 160 as seen in FIGS. 9 and 12.

Figure 13:
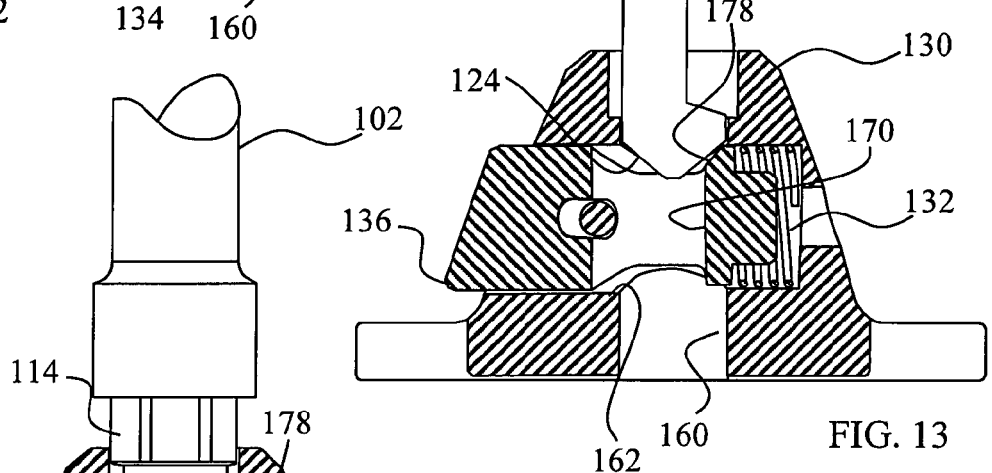
FIG. 13 depicts a cross sectional view of the head of FIG. 8 with the spring and restraining pin installed and the shuttle partially positioned within one of the bores of the base and the beveled portion of the shaft of FIG. 4 abutting the lip of the shuttle.

The base 130 is coupled to the shaft 102 by insertion of the beveled portion 124 into the bore 160 as shown in FIG. 13. As the beveled portion 124 approaches the intersection of the bores 160 and 162, the beveled portion 124 contacts the lip 178 thereby applying a compressive force on the spring 132. As the spring 132 is compressed, the shuttle 136 moves farther into the bore 162 (to the right as depicted in FIG. 13), bringing the coupling bore 170 into alignment with the bore 160.

Figure 14:
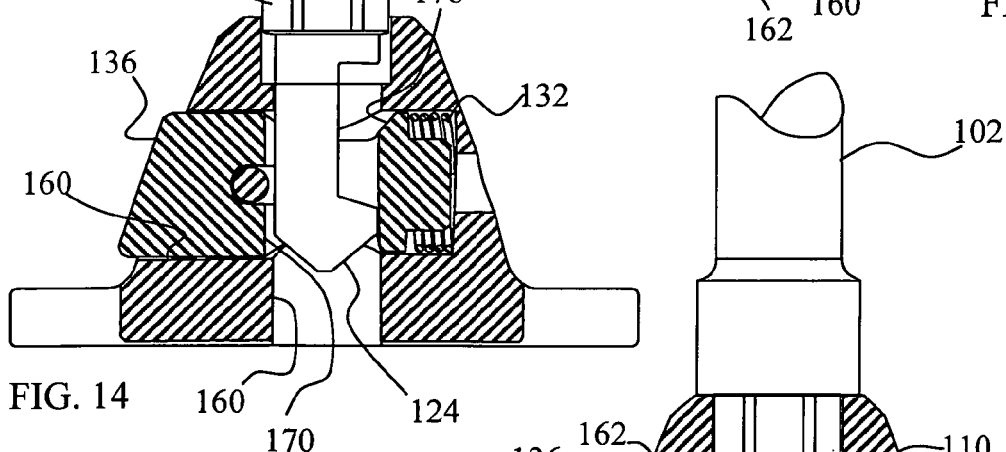
FIG. 14 depicts a cross sectional view of the head of FIG. 8 with the spring compressed and the restraining pin installed and the shuttle positioned more fully within one of the bores of the base as compared with FIG. 13 such that the coupling bore is aligned with one of the bores of the base allowing the beveled portion of the shaft of FIG. 4 to pass through the coupling bore.

Once the coupling bore 170 and the bore 160 are substantially aligned, the beveled portion 124 is allowed to move farther into the coupling bore 170 which is located at the intersection of the bores 160 and 162 as shown in FIG. 14. As shown in FIG. 14, the guide portion 114 of the shaft 102 begins to be received into the bore 160 before the beveled portion 124 is inserted into the portion of the bore 160 below the bore 162. The radius of the cylindrical portion of the perimeter of the guide portion 114 is selected to be slightly less than the radius of the cylindrical portion of the perimeter of the bore 160.

As shown in FIG. 9, the bore 160 includes a flat portion 164 that has an effective radius that is less than the radius of the cylindrical portion of the perimeter of the bore 160. Accordingly, the guide portion 114 can only be inserted into the bore 160 when the flat portion 116 of the guide portion 114 (see FIG. 7) is radially aligned with the flat portion 164 of the bore 160. This causes the coupling member 108 to be oriented in the coupling bore 170 as shown in FIG. 14.

Figure 15:
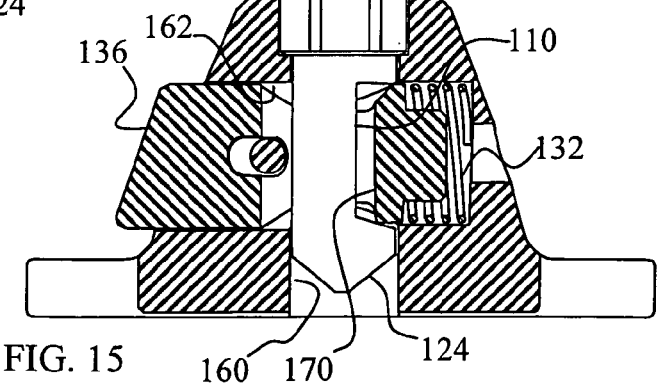
FIG. 15 depicts a cross sectional view of the head of FIG. 8 with the flange of the shuttle coupling with the indent of the shaft thereby coupling the shaft with the head.

Consequently, as the guide portion 114 is inserted into the bore 160, the indent 110 is oriented with the bore 162. Continued insertion of the shaft 102 into the base 130 causes the indent 110 to align with the bore 162 and the flange 176 as the beveled portion 124 moves into the portion of the bore 160 below the intersection with the bore 162. Since the beveled portion 124 is no longer contacting the shuttle 136 as shown in FIG. 15, the force of the spring 132 moves the shuttle 136 in a direction outwardly from the bore 162 causing the flange 176 to couple with the indent 110. The flange 176 thus axially locks the shaft 102 while the flat portion 164 of the bore 160 radially locks the shaft 102.

With the head 104 firmly coupled with the shaft 102, the constraining ring inserter system can be used to position a constraining ring. Referring to FIG. 16, the head 104 is aligned with the constraining ring 16 with the arms 138 and 140 over the constraining ring 16. The seating portion 154 is then placed against the constraining ring 16 and the head 104 is pressed and pivoted against the constraining ring 16 by movement of the head 104 in the direction of the arrows 182 and 184, respectively.

The constraining ring 16 has a diameter that is slightly less than the diameter of a cylinder shown as circle 186 in FIG. 17. A portion of the perimeter of the cylinder (depicted as circle 186) defines the seating portion 154. Accordingly, the constraining ring 16 initially fits within the constraining ring reception area defined by the arms 138 and 140 and against the ledge 159 as the head 104 is maneuvered in the direction of the arrows 182 and 184. The arms 138 and 140, however, are configured such that the gripper portions 150 and 152 lie within the perimeter of the circle 186. Thus, as the head 104 is pressed and rotated, the gripper portions 150 and 152 contact the constraining ring 16.

The arms 138 and 140, however, are somewhat flexible. The flexibility may be achieved by selection of the material used to fashion the arms 138 and 140, which may be any acceptable biocompatible material such as surgical grade stainless steel. Flexibility in the embodiment of FIG. 16 is further provided because the arms 138 and 140 are not joined at the distal portions 146 and 148.

In the embodiment of FIG. 16, the notches 156 and 158 provide even more flexibility. Accordingly, as the head 104 is pressed and rotated against the constraining ring 16, the gripper portions 150 and 152 are flexed outwardly from the positions shown in FIG. 17 to the position shown in shadow in FIG. 17, allowing the constraining ring 16 to slide into the constraining ring reception area as shown in FIGS. 18 and 19 and against the ledge 159. The resiliency of the arms 138 and 140 provide a gripping force on the constraining ring 16, keeping the constraining ring 16 within the constraining ring reception area.

The constraining ring 16 may now be positioned on the neck 30 in preparation for placement on the lip 22 as shown in FIG. 20. The shape of the shaft 102 is selected such that the shaft extends outwardly from the surgical site in a manner which does not overly interfere with the surgeon's access to the acetabular cup 12, the acetabular liner 14, or the femoral head 32. Once the surgeon is ready to lock the femoral head 32 within the cavity 24, the handle 106 is used to maneuver the constraining ring 16 into position and the ledge 159 transfers force uniformly about the constraining ring 16 to slide the constraining ring 16 onto the lip 22.

As the constraining ring 16 seats about the lip 22, sufficient force is exerted by the lip 22 on the constraining ring 16 to overcome the frictional grip of the arms 138 and 140 on the constraining ring 16. Accordingly, the surgeon can decouple the constraining ring inserter system 100 from the constraining ring 16.

Once the constraining ring inserter system 100 is decoupled from the head 104, the shaft 102 may be removed from the head 104 by depressing the button 180. This forces the shuttle 136 against the spring 132 thereby compressing the spring 132 and allowing the shuttle 136 to move more fully into the bore 162. The process described above for coupling the shaft 102 and the head 104 is then reversed and the shaft 102 is decoupled from the head 104. Decoupling of the head 104 and the shaft 102 facilitates decontamination and sterilization of the components.

Typically, acetabular systems incorporating constraining rings are used with femoral heads of different sizes. Thus, kits for use with femoral components may include constraining rings of different sizes. By way of example, a kit 200 shown in FIG. 21 includes a shaft 202 and five heads 204, 206, 208, 210 and 212. Each of the heads 204, 206, 208, 210 and 212 include a base 214, 216, 218, 220 and 222, respectively, which include bores and a shuttle that are identical to the bores and shuttles of the other bases. The bases 214, 216, 218, 220 and 222 couple with the handle 202 in the same manner as described above with respect to the shaft 102 and the base 130.

The heads 204, 206, 208, 210 and 212, however, are each configured to operate with a constraining ring of a size different than the size of the constraining ring with which the other heads are configured to operate. In this embodiment, the arms 224 and 226 of the head 204 are spaced apart so as to couple with a constraining ring of a 28 millimeter acetabular cup system, the arms 228 and 230 of the head 206 are spaced apart so as to couple with a constraining ring of a 32 millimeter acetabular cup system, the arms 232 and 234 of the head 208 are spaced apart so as to couple with a constraining ring of a 36 millimeter acetabular cup system, the arms 236 and 238 of the head 210 are spaced apart so as to couple with a constraining ring of a 40 millimeter acetabular cup system and the arms 240 and 242 of the head 212 are spaced apart so as to couple with a constraining ring of a 44 millimeter acetabular cup system.

Figure 21:
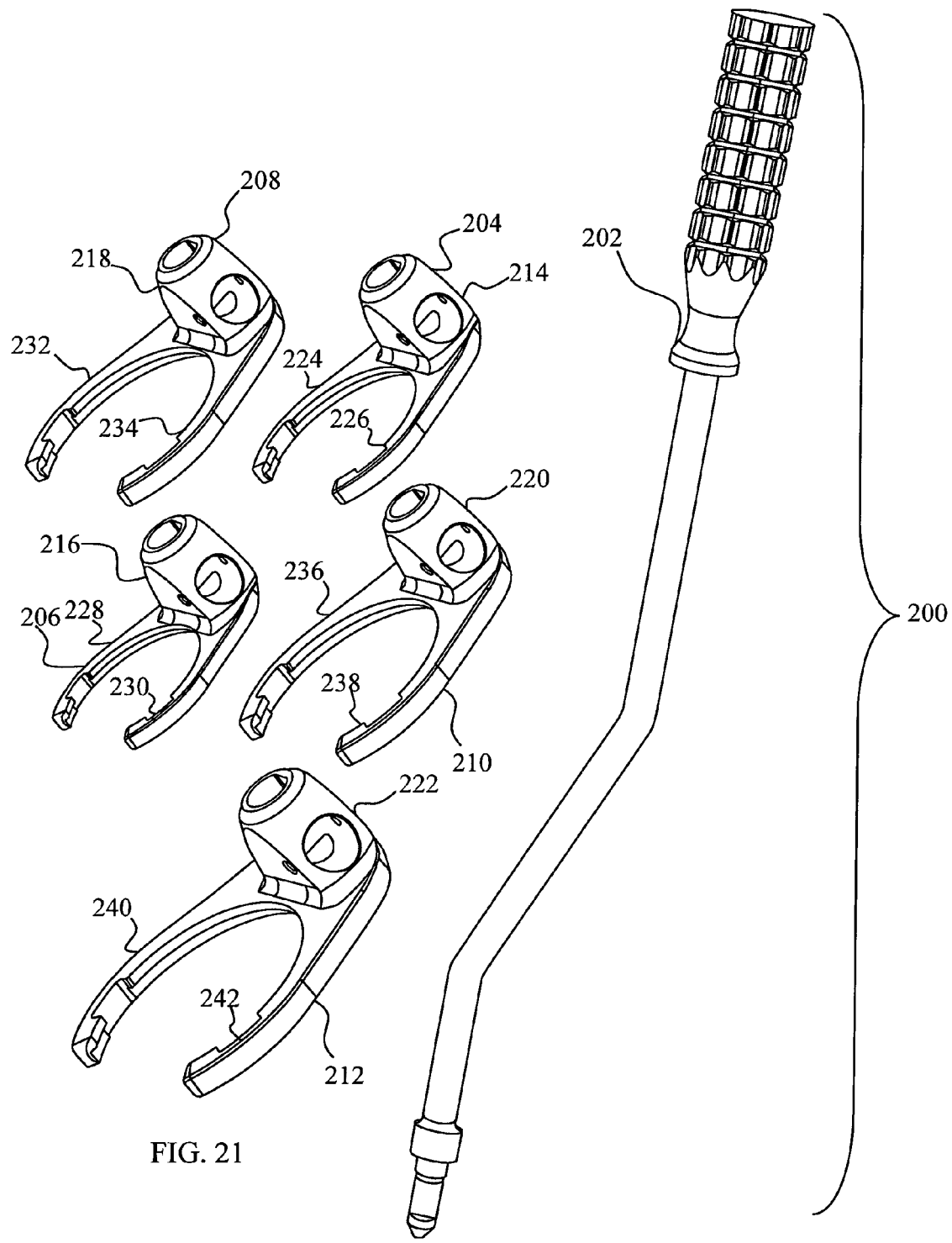
FIG. 21 depicts a perspective view of a kit including a shaft that can be used with each of a plurality of heads, each of the heads configured to be used with constraining rings provided with acetabular systems of different sizes in accordance with principles of the invention.

As discussed above, the flexibility of the arms for a particular head may be achieved in various ways. As the heads become smaller, however, the arms tend to become stiffer. For example, even when using the same materials, arms used for larger constraining rings are longer and thus provide more flexibility than the arms used with smaller constraining rings. In the embodiment of FIG. 21, the relative stiffness of the shorter arms such as the arms 224 and 226 is mitigated by increasing the size of the notch in the arms. Accordingly, the size of the notches in the arms of each of the heads 204, 206, 208, and 210 are larger than the notches in the next larger head.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A hand held instrument kit for use in positioning a constraining ring of an acetabular liner system comprising:
   a shaft including a first coupling member;
   a plurality of heads, each of the plurality of heads including a base configured to couple with the first coupling member and a pair of resilient gripper arms, each of the pair of resilient gripper arms defining a constraining ring reception area having a size different from the constraining ring reception area defined by the pair of gripper arms of each of the other of the plurality of heads; and
   a plurality of constraining rings, each constraining ring sized to be associated with a respective one of the constraining ring reception areas;
   wherein each of the constraining ring reception areas has a diameter that is slightly smaller than a diameter of a portion of the associated constraining ring, such that the portion may be resiliently received into the respective constraining ring reception area;
   wherein each resilient gripper arm includes a distal end portion and an intermediate portion located between the distal end portion and the base, and wherein the distal end portions of each pair of resilient gripper arms are spaced apart from each other by a distance that is less than a distance between the intermediate portions of the pair of resilient gripper arms; and
   wherein each of the plurality of constraining rings is sized to fit about the neck of an associated femoral implant utilized with the acetabular liner system.

2. The kit of claim 1, wherein the base of each of the plurality of heads comprises:
   a first bore sized to receive the first coupling member;
   a second bore intersecting the first bore; and
   a shuttle including a coupling bore configured to receive the first coupling member and movable within the second bore between a first position wherein the coupling bore is aligned with the first bore and a second position wherein the coupling bore is not aligned with the first bore.

3. The kit of claim 2, wherein the first bore of each of the plurality of heads is cooperatively keyed with the first coupling member 4. The kit of claim 2, each of the plurality of heads further comprising a biasing member operably connected to the shuttle to bias the shuttle toward the second position.

5. The kit of claim 1, wherein each of the plurality of heads further comprises:
   a ledge extending inwardly to a location directly above the constraining ring reception area defined by the pair of gripper arms.

6. The kit of claim 1, wherein:
   when the shaft is coupled with one of the plurality of heads the pair of resilient gripper arms of the one of the plurality of heads defines a plane; and
   the shaft is angled with respect to the plane.

7. The kit of claim 6, wherein the shaft further comprises:
   an upper portion extending along a first axis;
   a middle portion extending along a second axis, the second axis intersecting the first axis; and
   a lower portion extending along a third axis, the third axis intersecting the second axis.

8. The kit of claim 7, wherein the third axis is substantially parallel to the first axis.

9. The kit of claim 7, wherein the second axis forms an angle of between 15 and 30 degrees with the first axis.

10. The handheld instrument system of claim 9, wherein the second axis forms an angle of about 22.5 degrees with the first axis.

11. A handheld instrument system for insertion of a constraining ring onto an acetabular liner comprising:
a shaft including a first coupling member; and
at least one base member including a second coupling member for coupling with the first coupling member and a third coupling member configured to apply a gripping force on the constraining ring to couple the at least one base member with the constraining ring;
wherein the third coupling member comprises:
a pair of spaced apart gripper arms, each of the pair of spaced apart gripper arms including a gripping portion defining a constraining ring reception area and a ledge extending inwardly toward the other of the spaced apart arms to a location directly above the constraining ring reception area;
wherein each resilient gripper arm includes a distal end portion and an intermediate portion located between the distal end portion and the base, and wherein the distal end portions of each pair of resilient gripper arms are spaced apart from each other by a distance that is less than a distance between the intermediate portions of the pair of resilient gripper arms;
wherein the second coupler comprises:
a first bore sized to receive the first coupling member;
a second bore intersecting the first bore; and
a shuttle including a coupling bore configured to receive the first coupling member, the shuttle movable within the second bore between a first position wherein the coupling bore is aligned with the first bore and a second position wherein the coupling bore is not aligned with the first bore.

12. The handheld instrument system of claim 11, wherein:
the at least one base member comprises a plurality of base members;
the second coupling member of each of the plurality of base members is identical to the second coupling members of each of the other of the plurality of base members; and
the constraining ring reception area of each of the plurality of base members is of a size different than the size of the constraining ring reception area of each of the other of the plurality of base members.

13. The handheld instrument system of claim 11, wherein:
when the shaft is coupled with one of the plurality of base members the pair of spaced apart arms of the one of the plurality of base members defines a plane; and
the shaft is angled with respect to the plane.

14. The handheld instrument system of claim 13, wherein the shaft further comprises:
an upper portion extending along a first axis;
a middle portion extending along a second axis, the second axis intersecting the first axis; and
a lower portion extending along a third axis, the third axis intersecting the second axis.

15. The handheld instrument system of claim 14, wherein the third axis is substantially parallel to the first axis.

* * * * *